United States Patent [19]

Silver et al.

[11] Patent Number: 4,599,340

[45] Date of Patent: Jul. 8, 1986

[54] ENHANCED SOFT TISSUE FLAP SURVIVAL IN RECONSTRUCTIVE SURGERY

[75] Inventors: Lester Silver, Englewood, N.J.; Barry Goldenberg, New York, N.Y.

[73] Assignee: Miles Laboratories, Inc., Elkhart, Ind.

[21] Appl. No.: 731,363

[22] Filed: May 7, 1985

[51] Int. Cl.$^4$ .................. A61U 31/55; A61U 31/135; A61U 31/275; A61U 31/435; A61U 31/495
[52] U.S. Cl. ..................................... 514/277; 514/211; 514/255; 514/520; 514/650
[58] Field of Search ............... 514/277, 211, 255, 520, 514/650

[56] References Cited

PUBLICATIONS

Chem. Abst. 98—119164v (1983).

Primary Examiner—Stanley J. Friedman
Attorney, Agent, or Firm—Edward P. Gray

[57] ABSTRACT

A method for reducing soft tissue flap necrosis in a patient undergoing reconstructive surgery is disclosed. The method comprises administering to such patient an effective amount of a calcium channel blocking drug or a pharmaceutically acceptable non-toxic salt thereof to reduce said necrosis of said flap. Also disclosed are pharmaceutical compositions suitable for use in reducing soft tissue flap necrosis.

6 Claims, No Drawings

ENHANCED SOFT TISSUE FLAP SURVIVAL IN RECONSTRUCTIVE SURGERY

BACKGROUND OF THE INVENTION

Soft tissue flaps are used in reconstructive surgery in a variety of indications to correct a multitude of tissue defects. For example, flaps may be used to resurface a variety of wounds about the head, neck, extremities and trunk or they may be employed to cover exposed tendons, bones or major blood vessels. Flaps may be used about the face where color match and contour are important or they may be used to close wounds having a poor blood supply as where wound circulation would not support a skin graft. A flap traditionally refers to skin and subcutaneous tissue (or muscle, bone or other tissue) along with the entire vascular plexuses thus bringing a large supply of tissue and an intact blood supply to the site of injury. Modern surgical techniques have expanded the traditional definition of a flap to encompass free, microvascular flaps which may be anastomosed to an existing blood supply at or near the site of injury.

A persistent problem in the use of soft tissue flaps has been that of survival of the flap due to a diminished blood supply thus leading to a failure of the flap and a consequent unsatisfactory management of the wound. Various factors which influence the failure of these soft tissue flaps include extrinsic factors such as compression or tension on the flap, kinking of the pedicle, infection, hematoma, vascular disease, hypotension and abnormal nutritional states. Ischemia has also been postulated as playing a role in skin flap failure although the precise etiology has not been conclusively elucidated. For example, Reinisch (*Plastic and Reconstructive Surgery*, Vol. 54, pp 585–598, 1984) theorizes that the ischemia is due to the opening of A-V shunts with resultant non-nutritive blood flow to the effected area. On the other hand, Kerrigan (*Plastic and Reconstructive Surgery*, Vol. 72, pp 766–774, 1983) speculates that the ischemia is due to arterial insufficiency causing insignificant blood flow in the distal portion of the flap.

Because failure of these flaps can have deleterious consequences for the patient, various measures have been taken in the past to attempt to salvage failing flaps. Such measures include re-positioning the flap, topical cooling of the region, hyperbaric oxygen as well as the administration of various drugs. Among the drugs which have been used are dimethyl sulfoxide, histamine, isoxuprine and prostaglandin inhibitors. Additionally, various sympatholytic agents such as reserpine, phenoxybenzamine, propranolol guanethidine and 6-hydroxydopa have been used, as well as rheologic-altering agents such as dextran, heparin and pentoxifylline. Systemic steroids have been used in an attempt to increase body tolerance to ischemia, as has topical applications of flamazine. However, none of the treatment modalities or drugs used in prior attempts to reduce soft tissue flap necrosis have been entirely satisfactory or met with widespread acceptance in the medical community. Hence a need still exists for a means of reducing soft tissue flap necrosis (and the resultant failure of the flap) for use in reconstructive surgery.

SUMMARY OF THE INVENTION

The present invention is directed to a method for reducing soft tissue flap necrosis in a patient undergoing reconstructive surgery by administering to such patient an effective amount of a calcium channel blocking drug or a pharmaceutically acceptable non-toxic salt thereof to reduce said necrosis of said flap. Also disclosed are pharmaceutical compositions suitable for use in reducing soft tissue flap necrosis in reconstructive surgery containing an effective amount of a calcium channel blocking drug or a pharmaceutically acceptable non-toxic salt thereof, in combination with a pharmaceutically acceptable non-toxic inert diluent or carrier.

DETAILED DESCRIPTION OF THE INVENTION

As previously described soft tissue flaps play an important role in reconstructive surgery where the size of the wound, its location or underlying anatomical structures make primary suture either impracticable or impossible thus necessitating the transfer of tissue as a flap. As used herein, the phrase "soft tissue flap" is used in its broadest medical sense meaning a composite tissue having a self-sufficient blood supply typically though not necessarily from an underlying vascular plexus. Examples of such soft tissue flaps include traditional flaps such as skin and subcutaneous tissue, muscle, bone, pleura or peritoneum, small bowel stripped of mucosa and the like. Additionally, free microvascular flaps as mentioned earlier are intended within this meaning.

The calcium channel blocking drugs which may be used in the method of the present invention include the 1,4-dihydropyridines such as nitrendipine, nifedipine, nimodipine, nisoldipine and the like; $\beta$-phenethylamines such as tiapamil and verapamil; benzothiazepines such as diltiazem; ethylenediamines such as bepridil; and diaryl alkyl amines such as lidoflazine, prenylamine, fendiline, terodiline, cinnarizine and flunarizine. Of the calcium channel blocking drugs which may be used in the present invention, the 1,4-dihydropyridines are preferred. Of the 1,4-dihydropyridines, nitrendipine is particularly preferred for use in the method and pharmaceutical compositions of the present invention. Chemically, nitrendipine is 2,6-dimethyl-4-(3'-nitrophenyl)-1,4-dihydropyridine-3,5-dicarboxylic acid 3-methyl ester-5-ethyl ester.

The method of the invention is directed to the reduction of necrosis of soft tissue flaps in reconstructive surgery. The term "necrosis" as used herein is used in its generally accepted medical sense as meaning the death of more or less extensive groups of cells with degenerative changes in the intercellular substance thereby compromising survival of the soft tissue flap. Thus, by reducing the necrosis of the flap, the survivability of said flap is enhanced probably as a result of improved vascularity to the region which consequently leads to improved chances for ultimate healing of the wound. For these purposes, an effective amount of a calcium channel blocking drug or a combination of one or more calcium channel blocking drugs is administered. As used herein the term "effective amount" refers to that amount of one or a combination of one or more calcium channel blocking drugs necessary to reduce necrosis of a soft tissue flap. The skilled artisan will readily appreciate that the effective dosage ranges for the various calcium channel blocking drugs used in the methods and compositions of the present invention will vary widely particularly where the route of administration and the precise drug to be used are considerations. Of course other factors such as the size and age of the patient as well as the time and frequency of administration are to be considered in determining the dose in a given situation. Suffice it to say that the precise dose to be administered in a particular case will be either readily known from the published literature (inasmuch as these are all known compounds) or can be determined by conventional dose titration techniques. Typically though not necessarily the dosages may range anywhere from about 0.001 milligram (mg) per kilogram (kg) of body weight per day to about 12 mg per kg of body weight per day. For example, for the specific compound nitrendipine the dose may fall anywere within the range of from about 0.5 mg per kg of body weight per day to about 2 mg per kg of body weight per day. Preferably for nitrendipine the dose may range anywhere from about 1 mg per kg of body weight per day to about 1.5 mg per kg of body weight per day. Obviously, oral or topical dosages may be substantially higher than for a parenteral route of administration. The calcium channel blocking drug is administered to the patient when medically indicated, typically immediately following such surgery and is continued for several days thereafter.

The calcium channel blocking drug is administered internally or topically in the form of a pharmaceutical composition comprising one or more of said calcium channel blocking drugs or pharmaceutically acceptable non-toxic salts thereof in admixture with one or more pharmaceutically-acceptable non-toxic diluents or carriers, i.e., a diluent or carrier which is chemically inert to the drug and which has no detrimental side effects or toxicity under the conditions of use. Internal administration of the compounds may be parenteral as for example by intraperitoneal, subcutaneous or intravenous injection. Dosage forms for parenteral administration can be prepared by suspending or dissolving an amount of the drug in a non-toxic liquid vehicle suitable for injection such as an aqueous or oleaginous medium and sterilizing the suspension or solution. Alternatively, a measured amount of the drug may be placed in a vial and the vial and its contents sterilized and sealed. An accompanying vial or vehicle can be provided for purposes of mixing prior to administration. Pharmaceutical compositions adapted for parenteral administration employ diluents and carriers such as water and water-miscible organic solvents such as sesame oil, groundnut oil, aqueous propylene glycol and N,N'-dimethylformamide. Examples of such pharmaceutical compositions include sterile, isotonic, aqueous saline solutions of the calcium channel blocking drug which can be buffered with a pharmaceutically acceptable buffer and which are pyrogen free.

Internal administration of the calcium channel blocking drug may also be accomplished by means of oral pharmaceutical dosage forms. These include any of the conventional solid or liquid dosage forms such as powders, tablets, capsules, suspensions, solutions, syrups and the like including any sustained release preparations of the above. Such oral pharmaceutical dosage forms employ such ingredients as diluents and carriers, excipients and lubricants such as glucose, lactose, sucrose, corn and potato starch, sodium carboxymethylcellulose, ethyl cellulose, cellulose acetate, powdered gum tragacanth, gelatin, alginic acid, agar, stearic acid, sodium, calcium and magnesium stearates, sodium lauryl sulfate, polyvinylpyrrolidone, sodium citrate, calcium carbonate, dicalcium phosphate; as well as various buffering agents, surfactants, emulsifiers, dispersing agents, flavoring agents and the like.

Topical application of the calcium channel blocking drug may be had by incorporating said drug into ointments, creams, dressings, pastes, plasters and the like. Such pharmaceutical compositions can be prepared using various oleaginous, absorption or water soluble ointment bases as well as emulsion ointment bases, i.e., water-in-oil or oil-in-water bases. Examples of such bases include olive, cottonseed, sesame, persic and other fixed oils of vegetable origin; combinations of animal sterols such as cholesterol or other suitable lanolin fractions with white petrolatum; polyethylene glycol compounds including the semisolid preparations prepared through the use of bentonite, colloidal magnesium aluminum silicate, pectin, sodium alginate and the like. Various wetting agents, dispersing agents, emulsifiers, penetrants, emollients, detergents, hardeners or preservatives may also be used in the topical preparation.

Preparation of the internal or topical pharmaceutical compositions described herein may be readily achieved by one skilled in the art. Further information pertinent to the preparation of such compositions may be obtained by reference to standard treatises such as *Remington's Pharmaceutical Sciences,* Sixteenth Edition, Mack Publishing Co., Easton, Pa. (1980).

It is to be understood that the method of the present invention is not to be construed as limited by use of the term "reconstructive surgery" as that term applies to any specific medical specialty. Rather, the method of the invention is applicable to any surgical procedure involving a tissue transfer used to achieve maintenance of a wound which could not otherwise be satisfactorily maintained by techniques such as primary suturing, skin grafting and the like.

The following examples are intended to illustrate the present invention and are not be construed as a limitation thereon.

EXAMPLE 1

Twelve Sprague-Dawley rats weighing approximately 300–350 grams (g) each were divided into three groups of four rats each. The rats were anesthetized by the intraperitoneal injection of pentobarbital (4.5 mg/100g of body weight) prior to the elevation (i.e., physical uplifting and replacement) of a skin flap measuring 10 centimeters in length by 4 centimeters in width. The flap was designed based on the work of R. M. McFarlane et al (*Plastic and Reconstructive Surgery*, Vol. 35, No. 3, pp 245-262, 1965, which is incorporated herein by reference) with its base at the level of the inferior angle of the scapulae. The level of dissection was in the areolar tissue plane between the panniculus carnosus and the deep fascia.

A test solution of 0.4 mg of nitrendipine in 2.5 milliliters (ml) of DMSO was prepared. One rat in each group was designated as an untreated control, one rat was topically administered 2.5 ml of DMSO only, applied to the entire area of the flap and the remaining two rats were topically administered 2.5 ml of the test solution containing the nitrendipine (applied to the entire flap area). Each of the three groups of rats were then treated once-daily for seven days as above with the treatment for individual groups beginning at three postoperative stages: immediately following surgery, 24 hours after surgery, and 48 hours after surgery. The results of this test are set forth in Table I.

TABLE I

Effect of Topical Application of Nitrendipine on Skin Flap Survival[a]

| Initiation of Treatment[b] | Days of Treatment | Survival[c] |
|---|---|---|
| Immediately | 7 | 37 |
| 24 hours | 7 | 33.7 |
| 48 hours | 7 | 12.5 |

[a]Nitrendipine applied topically to entire skin flap at a concentration of 0.4 mg nitrendipine in 2.5 ml of DMSO.
[b]Time following surgical implantation of the flap when treatment began.
[c]Percent improvement in survival (i.e., wound healing) of the skin flaps relative to the untreated control.

The data shown in Table I clearly indicate that the topical application of nitrendipine had a positive influence on the survival of the skin flaps. In all groups, those animals administered DMSO alone (as well as the untreated controls) were not found to have a statistically significant increase in skin flap survival (data not shown).

EXAMPLE 2

The experimental design of Example 1 was again utilized to demonstrate the effect of parenteral administration of nitrendipine on skin flap survival. Twelve Sprague-Dawley rats (weighing approximately 300-350 g each) were divided into three treatment groups of four rats each. One rat of each group was designated as an untreated control, one rat received 2.5 ml of polyethylene glycol (PEG) 400 intraperitoneally and the remaining two rats were each administered (intraperitoneally) 0.4 mg of nitrendipine in 2.5 ml of a solution of PEG 400 and normal saline. The rats were anesthetized and the skin flaps were elevated and replaced in the donor bed as described in Example 1. The treatment regimen for each of the three groups of rats and the results of the study are shown in Table II.

TABLE II

Effect of Parenteral Administration of Nitrendipine on Skin Flap Survival[a]

| Initiation of Treatment | Doses Administered per Day | Days of Treatment | Survival[b] |
|---|---|---|---|
| Immediately prior to surgery | 1 | 1 | 48.1 |
| Immediately after surgery | 1 | 1 | 46.2 |
| Immediately after surgery | 1 | 5 | 95 |

[a]Nitrendipine administered intraperitoneally at a concentration of 0.4 mg nitrendipine in 2.5 ml of a solution of PEG 400 and normal saline.
[b]Percent improvement in survival (i.e., wound healing) of the skin flaps relative to the untreated control.

The data shown in Table II clearly demonstrate that nitrendipine is effective when administered parenterally in improving the survival of skin flaps. Particularly interesting is the treatment group which received one dose immediately after surgery followed by five days of treatment thereafter. In that group a 95 percent improvement in survival of the skin flaps relative to the untreated control was observed. In all groups those animals administered PEG 400 alone (as well as the untreated controls) were not found to have a statistically significant increase in skin flap survival (data not shown).

What is claimed is:

1. A method for reducing soft tissue flap necrosis in a patient undergoing reconstructive surgery which comprises administering to such patient an effective amount of a calcium channel blocking drug or a pharmaceutically acceptable non-toxic salt thereof to reduce said necrosis of said flap.

2. The method of claim 1 where the calcium channel blocking drug is a 1,4-dihydropyridine calcium channel blocking drug.

3. The method of claim 2 wherein the 1,4-dihydropyridine calcium channel blocking drug is nitrendipine.

4. The method of claim 3 wherein the nitrendipine is administered topically.

5. The method of claim 3 wherein the nitrendipine is administered parenterally.

6. The method of claim 5 wherein the parenteral route of administration is intraperitoneal.

* * * * *